(12) United States Patent
Sherman

(10) Patent No.: US 7,384,403 B2
(45) Date of Patent: Jun. 10, 2008

(54) WIRELESS COMMUNICATION SYSTEM FOR TRANSMITTING INFORMATION FROM A MEDICAL DEVICE

(75) Inventor: Jason T. Sherman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 157 days.

(21) Appl. No.: 11/016,295

(22) Filed: Dec. 17, 2004

(65) Prior Publication Data

US 2006/0136013 A1    Jun. 22, 2006

(51) Int. Cl.
*A61B 5/103* (2006.01)

(52) U.S. Cl. .................................... 600/587; 702/139

(58) Field of Classification Search ................. 607/30, 607/32, 33, 60, 61; 600/587; 702/139
See application file for complete search history.

(56) References Cited

U.S. PATENT DOCUMENTS

| | | | |
|---|---|---|---|
| 5,193,539 A * | 3/1993 | Schulman et al. ............. 607/61 |
| 5,197,488 A | 3/1993 | Kovacevic | |
| 5,360,016 A | 11/1994 | Kovacevic | |
| 5,425,775 A | 6/1995 | Kovacevic et al. | |
| 5,469,862 A | 11/1995 | Kovacevic | |
| 5,523,746 A * | 6/1996 | Gallagher ................. 340/5.61 |
| 5,545,191 A * | 8/1996 | Mann et al. ................. 607/57 |
| 5,626,630 A | 5/1997 | Markowitz et al. | |
| 6,628,989 B1 * | 9/2003 | Penner et al. ................. 607/59 |
| 6,631,296 B1 * | 10/2003 | Parramon et al. ............ 607/61 |
| 6,802,811 B1 | 10/2004 | Slepian | |
| 2002/0024450 A1* | 2/2002 | Townsend et al. ..... 340/870.16 |
| 2002/0177782 A1* | 11/2002 | Penner ....................... 600/485 |
| 2002/0177884 A1* | 11/2002 | Ahn et al. ................... 607/61 |
| 2003/0069644 A1 | 4/2003 | Kovacevic et al. | |
| 2003/0093503 A1 | 5/2003 | Yamaki et al. | |
| 2004/0019382 A1 | 1/2004 | Amirouche et al. | |
| 2004/0049245 A1* | 3/2004 | Gass et al. ................... 607/60 |

(Continued)

FOREIGN PATENT DOCUMENTS

WO      WO 92/17113      10/1992

(Continued)

OTHER PUBLICATIONS

National Semiconductoe LM62 2.7V, 15.6 mV/°C, SOT-23 Temperature Sensor, Jun. 1999 (7 pages) 2001 National Semiconductor Corporation Article.

(Continued)

*Primary Examiner*—Carl Layno
*Assistant Examiner*—Yun Haeng Lee
(74) *Attorney, Agent, or Firm*—Barnes & Thornburg LLP

(57) ABSTRACT

A medical device communication system may comprise a medical device and a wireless communication circuit mounted to the medical device. The wireless communication circuit is configured to broadcast information relating to the medical device. The medical device may be one of a surgical tool and an implant configured for subcutaneous implantation in a living biological body.

41 Claims, 4 Drawing Sheets

U.S. PATENT DOCUMENTS

| | | |
|---|---|---|
| 2004/0073279 A1 | 4/2004 | Malackowski |
| 2004/0113790 A1 | 6/2004 | Hamel et al. |
| 2005/0010299 A1 | 1/2005 | DiSilvestro |
| 2005/0010301 A1 | 1/2005 | DiSilvestro et al. |
| 2005/0010302 A1* | 1/2005 | Dietz et al. ............. 623/20.21 |

FOREIGN PATENT DOCUMENTS

| | | |
|---|---|---|
| WO | WO 2004/028627 | 4/2004 |
| WO | WO 2004/030757 | 4/2004 |
| WO | WO 2004/030759 | 4/2004 |

OTHER PUBLICATIONS

"Surgeon at Scripps Clinic Implants One-of-a-Kind "Electronic Knee"—Revolutionizing Research in Knee Implant Technology" (3 pages) Scripps Clinic Oct. 21, 2004 Article.

"Application Note" nRF24E1 and nRF24E2 RF layout nAN24-03 Jun. 2004 (6 pages) Nordic Semiconductor ASA (Revision 2.0).

* cited by examiner

WIRELESS COMMUNICATION SYSTEM FOR TRANSMITTING INFORMATION FROM A MEDICAL DEVICE

FIELD OF THE INVENTION

The present invention relates generally to systems for conducting wireless communications, and more specifically to such systems for transmitting information from medical devices such as medical instruments, medical implants, surgical tools and the like.

BACKGROUND

During the lifetime of a patient, it may be desirable to perform one or more surgical procedures on the patent as a result of, for example, disease or trauma. A number of medical implants and tools may be utilized during the performance of such a procedure.

SUMMARY

The present invention relates to systems for wirelessly transmitting information from medical devices such as medical instruments, medical implants, surgical tools and the like. The present invention may comprise one or more of the features recited in the attached claims, and/or one or more of the following features and combinations thereof. A medical device communication system may comprise a medical device being one of a surgical tool and an implant configured for subcutaneous implantation in a living biological body, and a wireless communication circuit. The wireless communication circuit may be mounted to the medical device and configured to broadcast information relating to the medical device.

The wireless communication circuit may include a memory unit having stored therein the information relating to the medical device. The memory unit may have stored therein program code for controlling operation of the wireless communication circuit. The wireless communication circuit may include a transceiver electrically connected to the memory unit, the transceiver configured to broadcast the information relating to the medical device. The wireless communication circuit may include an antenna electrically connected to the transceiver, wherein the transceiver broadcasts the information relating to the medical device via the antenna. The system may further include a circuit substrate mounted to the medical device. The circuit substrate may have the transceiver, memory unit and antenna mounted thereto. Alternatively, the circuit substrate may have the transceiver and memory unit mounted thereto, and the antenna may be mounted to the medical device remote from the circuit substrate. The system may further include a secondary coil circuit configured to inductively couple to a primary coil circuit to produce a DC voltage. The DC voltage produced by the secondary coil circuit may provide a supply voltage to the memory unit and to the transceiver. The system may further include a rechargeable voltage source providing a supply voltage to the memory unit and to the transceiver. In this embodiment, the DC voltage produced by the secondary coil circuit may provide a recharging voltage to recharge the rechargeable voltage source.

Alternatively or additionally, the medical device communication system may further include a sensor producing a sensor signal indicative of a physical property of the medical device, wherein the information relating to the medical device corresponds to the sensor signal. The wireless communication circuit may include a transceiver electrically connected to the sensor, wherein the transceiver is configured to broadcast the information relating to the medical device. The system may further include a circuit substrate mounted to the circuit substrate and having the transceiver and the sensor mounted thereto. Alternatively, the sensor may be mounted to the medical device remote from the circuit substrate. The wireless communication circuit may include an antenna electrically connected to the transceiver and mounted to the circuit substrate. The transceiver may broadcast the information relating to the medical device via the antenna. The wireless communication circuit may include a memory unit electrically connected to the transceiver and mounted to the circuit substrate. The memory unit may have stored therein program code for controlling operation of the wireless communication circuit. The memory unit may include a plurality of memory locations for storing information produced by the sensor. The wireless communication circuit may include an antenna electrically connected to the transceiver and mounted to the medical device remote from the circuit substrate, wherein the transceiver broadcasts the information relating to the medical device via the antenna. The system may further including a secondary coil circuit configured to inductively couple to a primary coil circuit to produce a DC voltage. The DC voltage produced by the secondary coil circuit may provide a supply voltage to the transceiver. The system may further include a rechargeable voltage source providing a supply voltage to the transceiver, and the DC voltage produced by the secondary coil circuit may provide a recharging voltage to recharge the rechargeable voltage source.

The medical device may be implanted in a living biological body in the form of a medical implant. The system may further include a primary coil circuit positioned outside of the biological body. The primary coil circuit may include a primary coil configured to inductively couple to a secondary coil included within the secondary coil circuit. The primary coil circuit may include an excitation source producing an AC excitation signal at in a frequency range selected to ensure inductive coupling between the primary and secondary coils. The primary coil may be responsive to the excitation signal to inductively couple to the secondary coil. The system may further include a cuff carrying the primary coil. The cuff may be configured to extend at least partially about a limb of the biological body with the primary coil positioned adjacent to the secondary coil.

These and other features of the present invention will become more apparent from the following description of the illustrative embodiments.

DESCRIPTION OF THE ILLUSTRATIVE EMBODIMENTS

Figure 1:
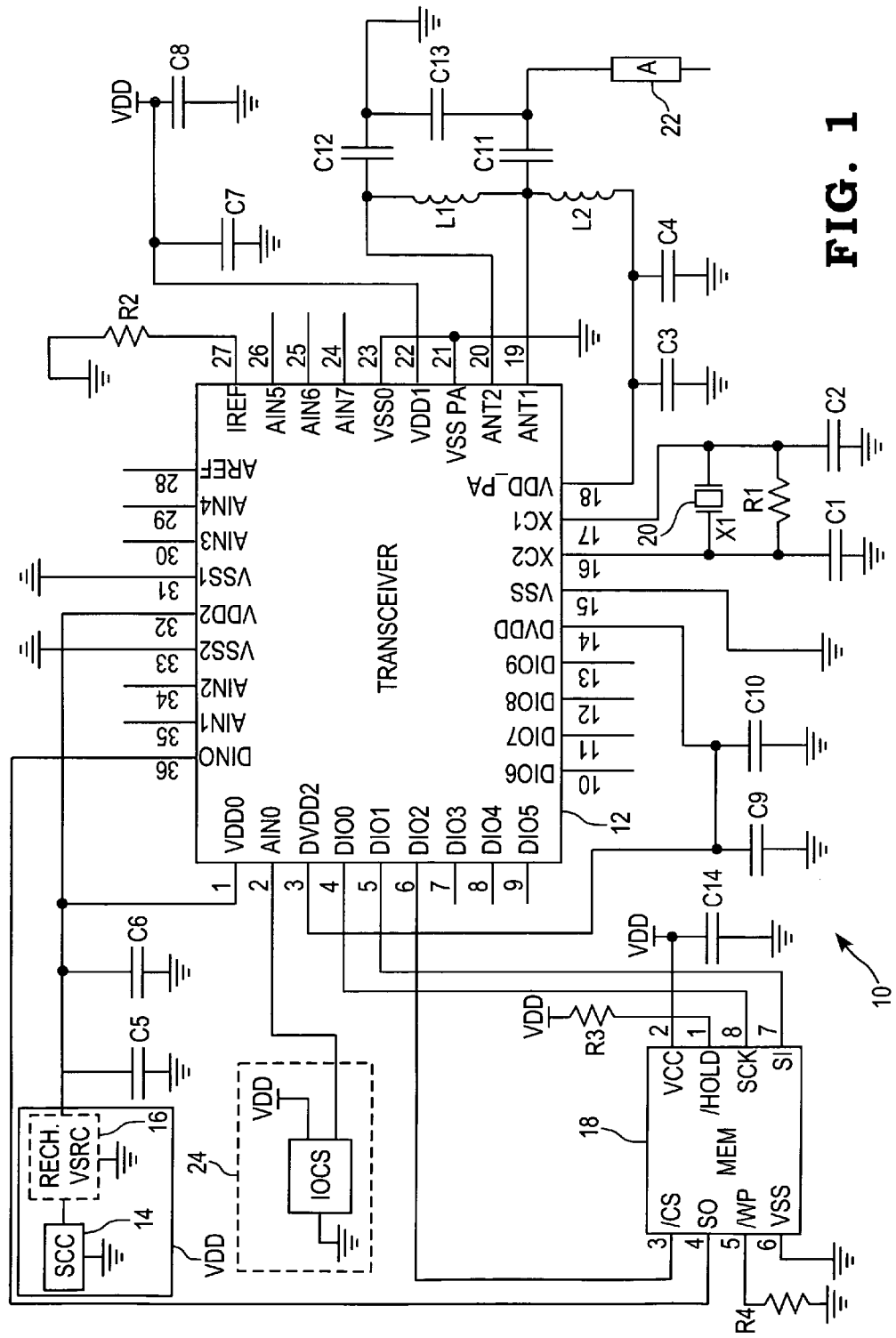
FIG. 1 is a schematic diagram of one illustrative embodiment of a wireless communications circuit for transmitting information from a medical device.

For the purposes of promoting an understanding of the principles of the invention, reference will now be made to a number of illustrative embodiments illustrated in the drawings and specific language will be used to describe the same.

Referring now to FIG. 1, a schematic diagram of one illustrative embodiment of a wireless communication circuit 10 for transferring information from a medical device is shown. Central to the communication circuit 10 is a transceiver circuit 12 operable to broadcast information using conventional wireless communications technology. The transceiver circuit 12 may be, for example, an nRF241 E1, 2.4 GHz RF transceiver/transmitter that is commercially available through Nordic Semi-Conductor ASA of Tiller, Norway, although the present disclosure contemplates that the transceiver circuit 12 may alternatively be any known transceiver circuit capable of broadcasting information in the radio frequency range (e.g., 402-405 MHz or so-called MICS band) or other frequency range including, but not limited to, sub radio frequencies. The transceiver circuit 12 operates at a supply voltage, VDD, and at a clock frequency generated by a conventional crystal 20. The crystal 20 in the illustrated embodiment is a 16 MHz crystal, although crystals operating at other clock frequencies may be used.

The wireless communication circuit 10 further includes a voltage source block supplying the operating voltage VDD. In one embodiment, for example, the voltage source may be provided in the form of a conventional secondary coil circuit 14 configured to inductively couple to a conventional primary coil circuit. In this embodiment, the secondary coil circuit includes a conventional secondary inductive coil that is electrically connected to a conventional AC-to-DC conversion circuit. When an energized primary coil (not shown) inductively couples with the secondary coil, an AC voltage is induced in the secondary coil according to known physical principles. The induced AC voltage is converted to the supply voltage, VDD, by the AC-to-DC conversion circuit. This DC output voltage may be applied directly to the VDD supply line (e.g., VDDO and VSS2), or may alternatively be provided to a rechargeable voltage source 16 interposed between the secondary coil circuit 14 and the operating voltage supply line as shown in phantom in FIG. 1. In the former case, the wireless communication circuit 10 has no internal voltage source, and may be activated for operation only when the secondary coil circuit 14 is inductively coupled to an activated primary coil circuit, one example of which will be described hereinafter with respect to FIG. 3. In the later case, the rechargeable voltage source 16 is operable to produce the operating supply voltage, VDD, for some time period between recharging events. In this embodiment, however, a the secondary coil circuit 14 must be periodically coupled to an activated primary coil circuit so that the secondary coil circuit 14 produces the DC supply voltage, VDD, for a sufficient time to recharge the rechargeable voltage source 16.

In the embodiment illustrated in FIG. 1 wherein the transceiver circuit 12 is a nRF241 E1, 2.4 GHz RF transceiver/transmitter produced by Nordic Semi-Conductor, such an RF transceiver does not include sufficient memory for storage of program code and/or any generated data. Accordingly, a separate memory unit 18 is provided for the purpose of storing one or more executable algorithms and/or storing data. In the illustrative embodiment, the circuit 18 is a 4.0 Kbyte serial EEPROM that is commercially available through any number of semiconductor manufacturers. In other embodiments, the transceiver circuit 12 may include sufficient on-board memory, in which case the memory circuit 18 may be omitted.

In the illustrated embodiment, the wireless communication circuit 10 is configured for short-range wireless communication, and in this regard a single-ended antenna 22 is connected via a differential-to-single ended matching network, comprising L1, L2, C3-C4 and C11-C13 to differential antenna inputs, ANT1 and ANT2, of the transceiver circuit 12. In the illustrated embodiment, the antenna 22 is a 50 OHM antenna that may be implemented in any variety of known antenna configurations.

The wireless communication circuit 10 may include one or more sensors producing sensor signals indicative of one or more corresponding operating conditions of the medical device with which the wireless communication circuit 10 is associated. For example, the wireless communication circuit 10 may be mounted to a medical implant that is then subsequently implanted to biological tissue. In this case, one or more sensors may be suitably positioned relative to the medical implant to provide one or more corresponding sensor signals indicative of one or more corresponding operating characteristics of the implant. Examples of such operating characteristics may include, but are not limited to, temperature, load, strain, torque and the like. As another example, the wireless communication circuit 10 may be mounted to a surgical instrument. In this case, one or more sensors may be suitably positioned relative to the surgical instrument to provide one or more corresponding sensor signals indicative of one or more corresponding operating parameters of the surgical instrument. Examples of such operating parameters may include, but are not limited to, implement (e.g., saw, drill, etc.) speed, implement position, implement operating direction, instrument operating temperature, and the like. In the illustrated embodiment, the wireless communication circuit 10 includes a general operating condition sensor (OCS) 24, which may be or include any sensor of the foregoing type that is electrically connected to one of the analog inputs, e.g., AIN0, of the transceiver circuit 12. Sensory data produced by the sensor 24 may be routed by the transceiver circuit 12 to the memory circuit 18 for storage therein and subsequent wireless transmission via the antenna 22 to a suitable receiving circuit separate from the medical device. Alternatively, the transceiver circuit 12 may be operable to transmit the sensory data in real time via the antenna 22 in a conventional manner.

The remaining electrical components illustrated in FIG. 1 are provided to support operation of the transceiver circuit 12 and memory circuit 18. Typical values of the illustrated components for one specific implementation of the wireless communication circuit 10 are provided in the following Table 1. In this specific implementation of the wireless communication circuit 10, the rechargeable voltage source 16 is not included, and the operating condition sensor 24 is implemented as a single temperature sensor. It will be understood that such component values are provided only way of example, and that other component values may be used.

TABLE 1

| Component Identification | Description | Physical Size | Value | Tolerance | Units |
|---|---|---|---|---|---|
| C1 | Ceramic Capacitor, 50 V, NPO | 0603/0402 | 22 | ±5% | pF |
| C2 | Ceramic Capacitor, 50 V, NPO | 0603/0402 | 22 | ±5% | pF |
| C3 | Ceramic Capacitor, 50 V, NPO | 0603/0402 | 22 | ±5% | pF |
| C4 | Ceramic Capacitor, 50 V, X7R | 0603/0402 | 2.2 | ±10% | nF |
| C5 | Ceramic Capacitor, 50 V, X7R | 0603/0402 | 1.0 | ±10% | nF |
| C6 | Ceramic Capacitor, 50 V, X7R | 0603/0402 | 10 | ±10% | nF |
| C7 | Ceramic Capacitor, 50 V, X7R | 0603/0402 | 10 | ±10% | nF |
| C8 | Ceramic Capacitor, 50 V, X7R | 0603/0402 | 1.0 | ±10% | nF |
| C9 | Ceramic Capacitor, 50 V, X7R | 0603/0402 | 1.0 | ±10% | nF |
| C10 | Ceramic Capacitor, 50 V, X7R | 0603/0402 | 33 | ±10% | nF |
| C11 | Ceramic Capacitor, 50 V, NPO | 0603/0402 | 1.0 | ±0.25 pF | pF |
| C12 | Ceramic Capacitor, 50 V, NPO | 0603/0402 | 1.0 | ±0.25 pF | pF |
| C13 | Ceramic Capacitor, 50 V, NPO | 0603/0402 | 1.5 | ±0.25 pF | pF |
| C14 | Ceramic Capacitor, 50 V, X7R | 0603/0402 | 10 | ±10% | nF |
| L1 | Inductor, wire wound | 0603/0402 | 3.6 | ±5% | nH |
| L2 | Inductor, wire wound | 0603/0402 | 22 | ±5% | nH |
| R1 | Resistor | 0603/0402 | 1.0 | ±1% | Mohm |
| R2 | Resistor | 0603/0402 | 22 | ±1% | Kohm |
| R3 | Resistor | 0603/0402 | 10 | ±1% | Kohm |
| R4 | Resistor | 0603/0402 | 10 | ±1% | Kohm |
| 12 | nRF241E1 (Nordic VLSI) | QFN36/ 6 × 6 | | | |
| 18 | 4 Kbyte serial EEPROM with SPI interface | SO8 | 2XX320 | | |
| 20 | Crystal, $C_L$ = 12 pF, ESR <100 ohm | L × W × H = 4.0 × 2.5 × 0.8 | 16 | +/−30 ppm | MHz |
| 24 | LM62 2.7 V, 15.6 mV/° C. Temperature Sensor (National Semiconductor) | SOT-23 | | | |

Figure 2:
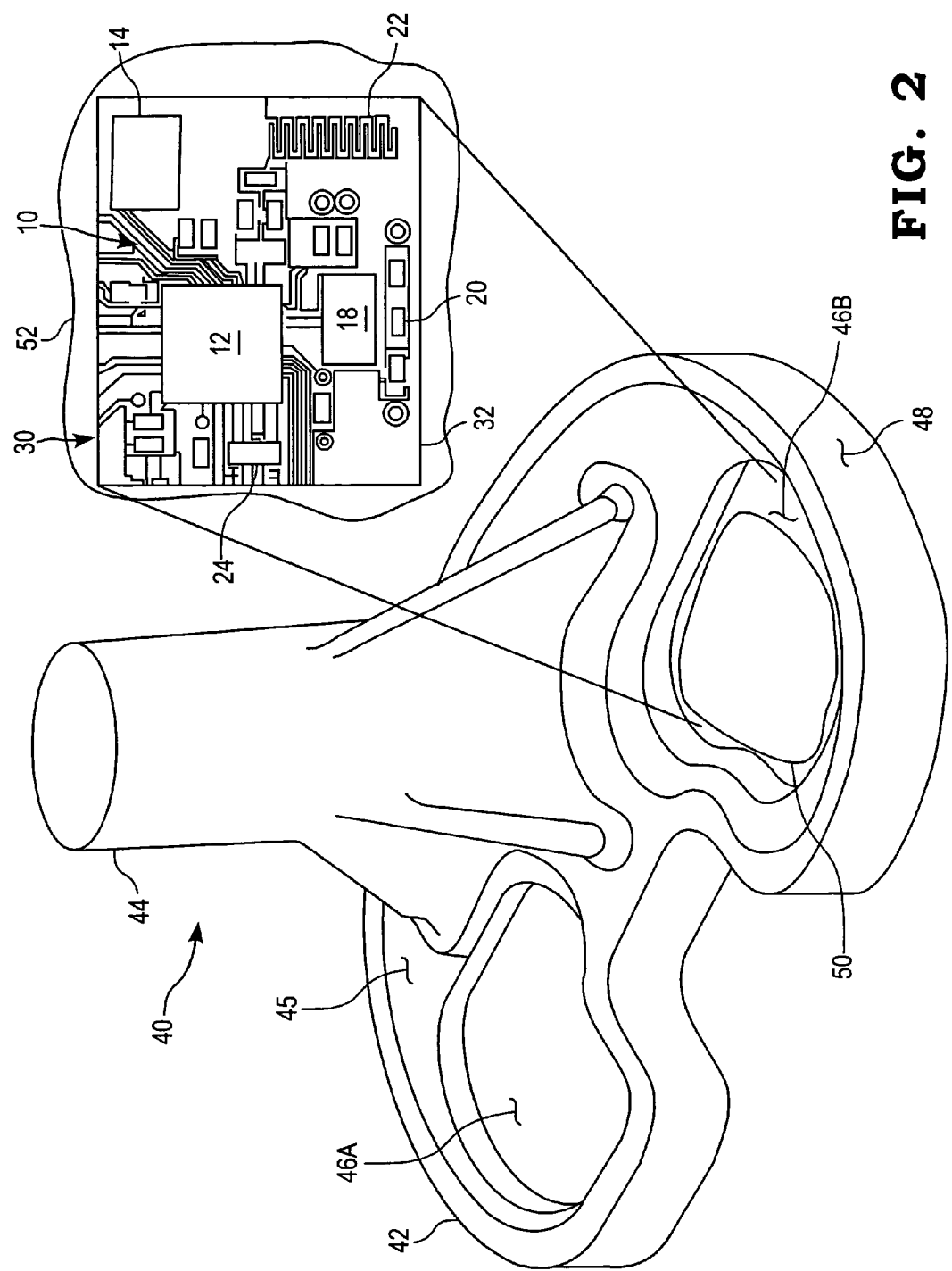
FIG. 2 is an exploded perspective view showing one arrangement for mounting one illustrative implementation of the wireless communications circuit of FIG. 1 to a medical implant.

Referring now to FIG. 2, an exploded perspective view of one arrangement for mounting one illustrative physical implementation 30 of the wireless communication circuit 10 of FIG. 1 to a medical implant 40 is shown. In the illustrated embodiment, the wireless communication circuit 10 of FIG. 1 is physically implemented in the form 30 of a printed circuit board (PCB) 32 having a number of integrated circuits (ICs) and discrete electrical components mounted thereto. For example, the physical implementation 30 of the wireless communication circuit 10 illustrated in FIG. 2 shows the transceiver circuit 12, secondary coil circuit 14, memory circuit 18, crystal 20, antenna 22 and implant operating condition sensor 24, as well as the number of additional discrete components, mounted to the printed circuit board 32. The implementation illustrated in FIG. 2 does not include a rechargeable voltage source 16 as depicted in phantom in FIG. 1, although it should be understood that other implementations of the wireless communication circuit 10 may include such a rechargeable voltage source 16. It will be understood that the physical implementation 30 of the wireless communication circuit 10 shown in FIG. 2 represents only one example implementation, and that any one or more of the circuit components mounted to the printed circuit board 32 may alternatively be mounted to the medical implant remote from the printed circuit board 32. It should also be understood that the physical implementation 30 of the wireless communication circuit 10 illustrated in FIG. 2 is not intended to depict an actual working layout of the circuit components, but rather to illustrate that the wireless communication circuit 10 is physically realizable in the form of a number of integrated circuits and discrete electrical components mounted to a conventional printed circuit board 32. Alternatively, the wireless communication circuit 10 may be physically implemented in the form of one or more integrated circuits and/or discrete components mounted to one or both sides of a conventional flexible circuit substrate, a multi-layer circuit board or circuit substrate, or surface mounted to a conventional circuit substrate. Alternatively still, two or more components of the wireless communication circuit 10 may be physically implemented in the form of a single application specific integrated circuit (ASIC) that may or may not be mounted to a circuit board or substrate prior to being mounted to the medical implant 40.

In the illustrated embodiment, the medical implant 40 is shown in the form of a conventional tibial tray having a base 42 and a stem 44 extending away from one face 45 of the base 42. The face 45 of the tibial tray defines a pair of recesses 46A and 46B therein. In accordance with a conventional implant procedure, a proximal portion of a human tibia is removed to provide a planar surface relative to the knee, and the stem 44 of the tibial tray 40 then extends into the tibia with the face 45 of the tray member 42 contacting the now planar surface of the modified tibia. It will be understood that while the medical implant 40 is illustrated in the form of one component of a knee prosthesis, the medical implant 40 may alternatively be any medical implant, or component of a medical implant, configured for subcutaneous implantation in a living biological body.

The physical implementation 30 of the wireless communication circuit 10 of FIG. 1 may be mounted to any convenient surface of the medical implant 40. In the embodiment illustrated in FIG. 2, for example, the printed circuit board 32 is sized to be mounted within the recess 46B defined in the face 45 of the tray member 42. Alternatively, the print circuit board 32 could be mounted within the recess 46A of the tray member 42. In any case, the printed circuit board 32 is mounted to the tray member 42 via a suitable adhesive 50 dispensed in the recess 46B as illustrated in FIG. 2. In many cases, as is the case with the tibial tray 40, the implant is formed of a metal composite, and is therefore electrically conductive. Likewise, the underside surface of the printed circuit board 32 may define a number of electrically conductive circuit lines and/or electrical components. In such cases, it is accordingly desirable to either provide an electrically insulated member between the circuit board 32 and the implant 40, or to use an adhesive 50 that is electrically non-conductive and ensure that the underside of the printed circuit board 32 does not contact the electrically conductive surface of the implant 40. In other embodiments, the wireless communication circuit 10 may be implemented either as a single application specific integrated circuit or as a number of integrated circuits and discrete electrical components, surface-mounted in a conventional manner to an electrically insulating substrate, e.g., alumina or other ceramic substrate. In such cases, the underside of such a substrate typically will not include any electrically-conductive components, and may therefore be mounted to the medical implant 40 using any desired adhesive and/or conventional attachment structures.

With the physical implementation 30 of the wireless communication circuit 10 mounted to the medical implant 40 as just described, it may be desirable to provide one or more biocompatible passivation layers 52 to the top surface of the physical implementation 30. Such one or more passivation layers 52 should be provided in the form of a composition that is both bio-compatible and fluid/tissue impervious to thereby isolate the circuit components from bodily fluids and tissue.

It should be noted that in the embodiment illustrated in FIG. 2, the antenna 22 is arranged in a serpentine configuration and is mounted to the printed circuit board 32. Alternatively, the antenna 22 may be provided in the form of any conventional antenna configuration, and/or may be mounted to another surface of the medical implant 40, such as the side surface 48 of the tray member 42, to thereby optimize data broadcast from the wireless communication circuit 10.

Figure 3:
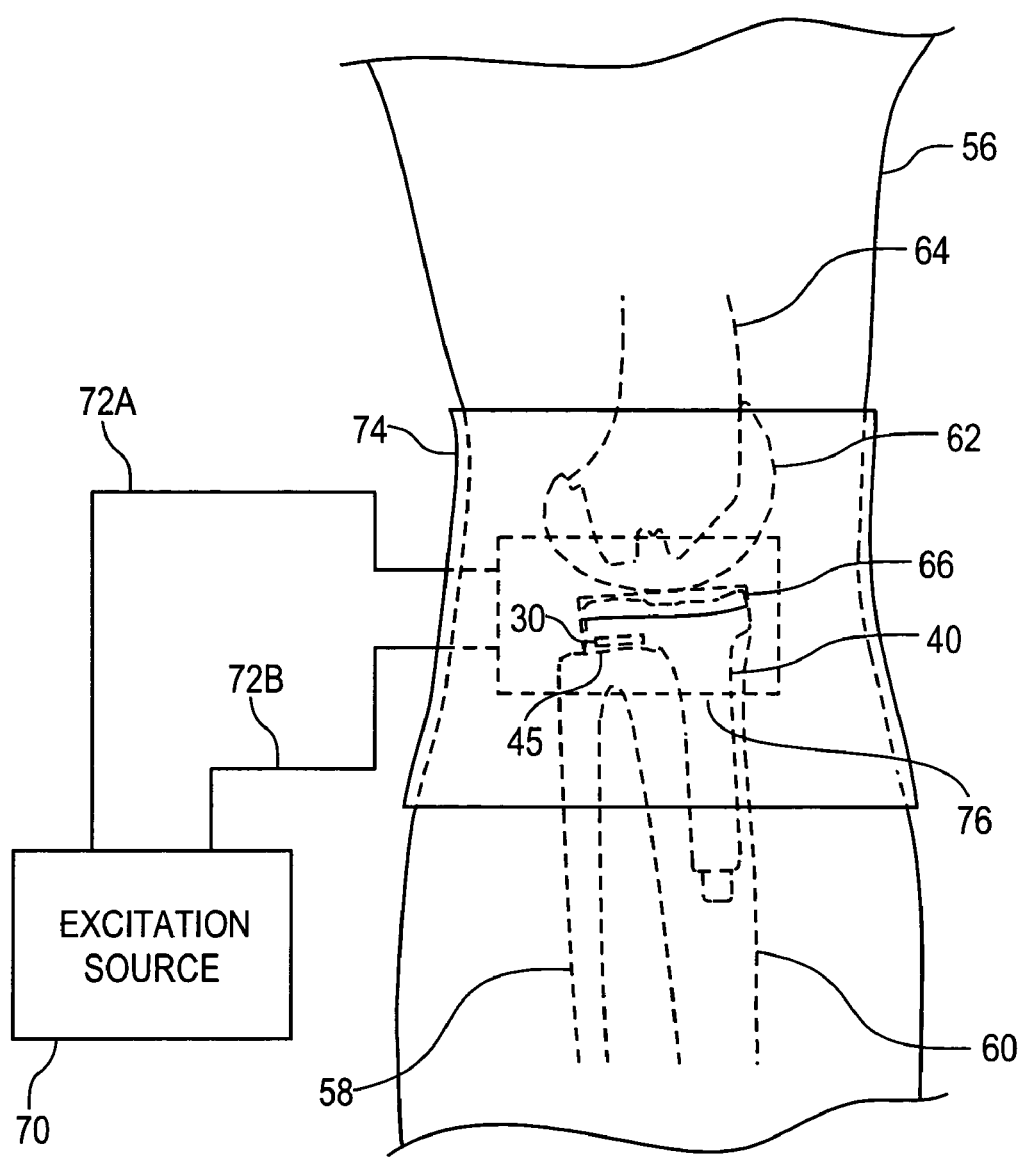
FIG. 3 is a diagrammatic illustration of a circuit arrangement for supplying an operating voltage to, or for recharging a rechargeable voltage source associated with, the wireless communications circuit of FIG. 1 mounted to an implanted medical device.

Referring now to FIG. 3, a diagrammatic illustration of a circuit arrangement for supplying an operating voltage to, or for recharging a rechargeable voltage sources associated with, the physical implementation 30 of the wireless communication circuit 10 of FIG. 1 is shown. In the illustrated embodiment, the medical implant 40 is the tibial tray of FIG. 2 mounted to a prepared tibia 60 (and fibula 58) as described hereinabove with the face 45 of the tibial tray 40 in contact with the prepared surface of the tibia 60 and fibula 58. A femoral component 62 is similarly mounted to a prepared end of a femur 64 adjacent to the prepared end of the tibia 60, and a conventional bearing insert 66 is mounted to the proximal surface of the tibial tray 40 and thereby interposed between the tibia tray 40 and the femoral component 62. As illustrated in FIG. 3, the physical implementation 30 of the wireless communication circuit 10 is mounted to the tibial tray 40 as described hereinabove with respective to FIG. 2, and is thus carried by the tibial tray 40 within a patient's leg 56 as shown in FIG. 3. An excitation source 70 is electrically connected via signal paths 72A and 72B to a primary inductive coil 76 inserted into and carried by a cuff 74. The cuff 74 is configured to be slidably received over the patient's leg 56 so that the primary coil 76 is positioned over and adjacent to the physical implementation 30 of the wireless communication circuit 10, as shown in FIG. 3, and thereby over and adjacent to the secondary coil within the secondary coil circuit 14. The excitation source 70 includes conventional signal conditioning circuitry configured to process an AC voltage signal from a suitable source, e.g., conventional building wiring coupled to a service panel, to supply excitation signals to the primary coil in a suitable frequency range. The frequency range will generally be selected, as a function of the distance between the primary coil 76 and the secondary coil within the implanted secondary coil circuit 14, to be in a frequency range that ensures inductive coupling between the primary coil 76 and the secondary coil within the secondary coil circuit 14. As described hereinabove, the secondary coil circuit 14 produces a DC supply voltage, VDD, when inductively coupled to an activated or energized primary coil 76, and the supply voltage, VDD, is used either to supply the operating supply voltage, VDD, directly to the circuit 10 or to recharge a rechargeable VDD voltage source 16.

Figure 4:
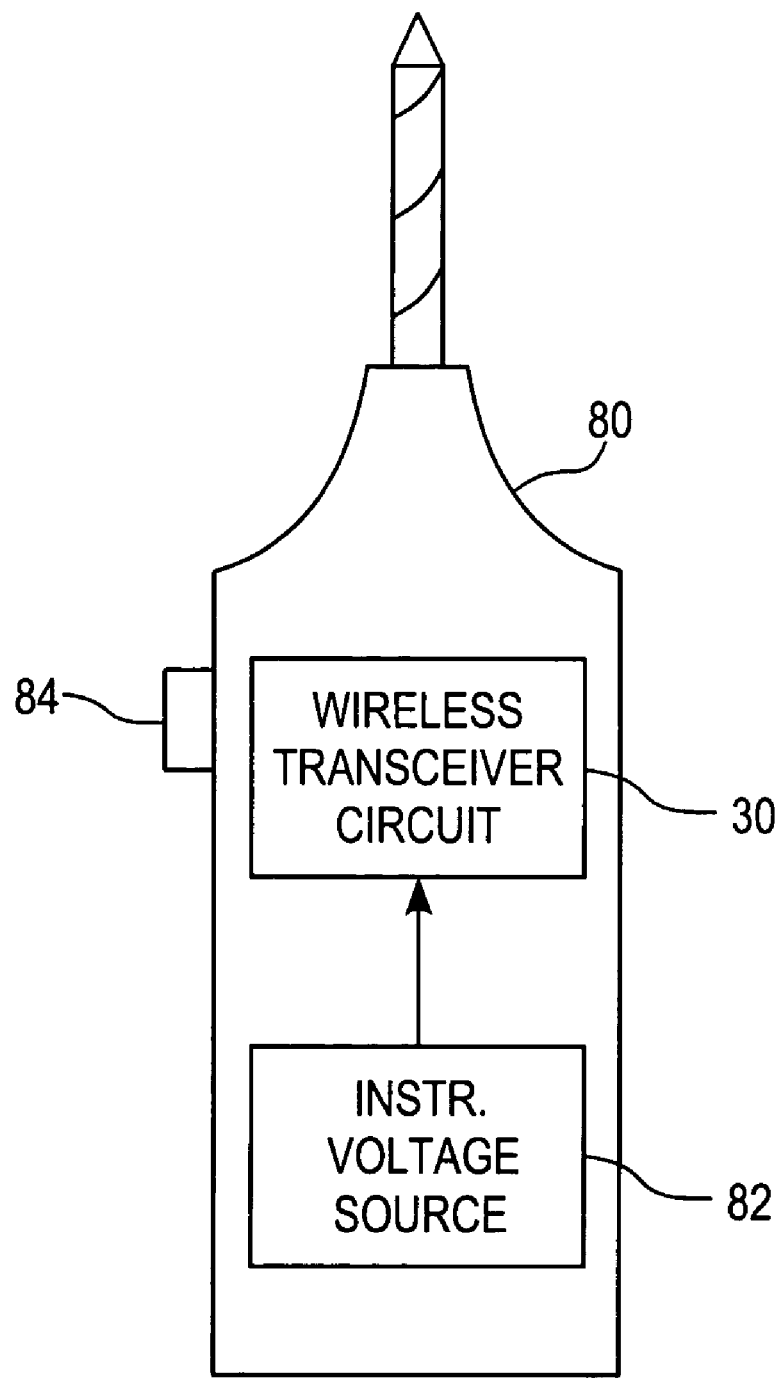
FIG. 4 is a schematic diagram of one illustrative embodiment of a medical instrument including the wireless communication circuit of FIG. 1.

Referring now to FIG. 4, a schematic diagram of one illustrative embodiment of a medical instrument 80 that includes therein the physical implementation 30 of the wireless communication 10 of FIG. 1 is shown. In the illustrated embodiment, the physical implementation 30 of the wireless communication circuit 10 does not include either of the secondary coil circuit 14 or the rechargeable voltage source 16, and instead receives its operative supply voltage, VDD, from a conventional voltage source 82 carried by the medical instrument 80. Otherwise, the wireless communication circuit 10 may be as described as hereinabove with respect to FIG. 1, and may include any one or more sensors producing sensory information relating to the identify and/or operation of the medical instrument 80. While the medical instrument 80 is illustrated in FIG. 4 as being a conventional surgical drill, it will be understood that for the purpose of this document the medical instrument 80 may alternatively be any medical instrument, surgical tool or the like that includes one or more electrically acutatable implements such a s a saw, drill or the like, or that does not include any one or more electrically actuatable implements.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, details relating to another medical device system are set forth in U.S. patent application Ser. No. 10/887,766, which is assigned to the assignee of the present invention, and the disclosure of which is incorporated herein by reference.

What is claimed is:

1. A medical device comprising:
   an orthopaedic implant comprising a tray to contact a bone and a stem to extend into the bone, the tray comprising a recess;
   a circuit board positioned in the recess of the orthopaedic implant tray;
   a sensor mounted on the circuit board and configured to produce a sensor signal indicative of an operating condition of the orthopaedic implant;
   a memory unit mounted on the circuit board and electrically coupled to the sensor; and
   a transmitter mounted to the circuit board and electrically coupled to the sensor and the memory unit, the transmitter configured to broadcast the sensor signal.

2. The medical device of claim 1, wherein the memory unit comprises a plurality of memory locations for storing sensor signals produced by the sensor.

3. The medical device of claim 1, wherein the memory unit has stored therein program code for controlling the operation of the transmitter.

4. The medical device of claim 1, further comprising an antenna electrically coupled to the transmitter and remotely located from the circuit board.

5. The medical device of claim 4, wherein the antenna is mounted to the orthopaedic implant.

6. The medical device of claim 1, further comprising a secondary coil circuit configured to be inductively coupled to a primary coil circuit to produce a DC voltage, wherein the DC voltage provides a supply voltage to the memory unit and to the transmitter.

7. The medical device of claim 1, further comprising:
   a secondary coil circuit configured to be inductively coupled to a primary coil circuit to produce a DC voltage; and
   a rechargeable voltage source configured to provide a supply voltage to the memory unit and the transmitter, wherein the DC voltage produced by the secondary coil circuit provides a recharging voltage to recharge the rechargeable voltage source.

8. The medical device of claim 1, further comprising:
   a secondary coil circuit configured to be inductively coupled to a primary coil circuit to produce a DC voltage; and
   a cuff configured to receive a limb of a patient such that the cuff extends at least partially about the limb, the cuff carrying a primary coil of the primary coil circuit and configured to be positioned on the patient such that the primary coil and a secondary coil of the secondary coil circuit inductively couple while the primary coil is activated.

9. The medical device of claim 1, further comprising a secondary coil circuit configured to be inductively coupled to a primary coil circuit to produce a DC voltage, wherein the primary coil circuit includes a primary coil and an excitation source electrically coupled to the primary coil, the excitation circuit producing an AC excitation signal at a frequency selected to ensure inductive coupling between the primary and secondary coils.

10. The medical device of claim 1, further comprising an insulating layer positioned over the circuit board and configured to insulate the transmitter and memory unit from biological material.

11. The medical device of claim 1, wherein the sensor is selected from a group consisting of a temperature sensor, a load sensor, a strain sensor, and a torque sensor.

12. The medical device of claim 1, wherein the circuit board is secured to the orthopaedic implant using an electrically non-conductive adhesive.

13. The medical device of claim 1, wherein the transmitter is configured to continually broadcast the sensor signal.

14. The medical device of claim 1, wherein the transmitter is configured to store the sensor signal in the memory unit.

15. The medical device of claim 14, wherein the transmitter is configured to broadcast the sensor signal after the sensor signal has been stored in the memory unit.

16. A medical implant comprising:
   a tibial tray to contact a planarized surface of a tibia, the tray comprising a plurality of recesses;
   a circuit board positioned in a recess of the plurality of recesses of the tibial tray;
   a sensor mounted on the circuit board and configured to produce a sensor signal indicative of an operating condition of the implant;
   a transmitter mounted on the circuit board and electrically coupled to the sensor; and
   an antenna electrically coupled the transmitter and remotely located from the circuit board.

17. The medical implant of claim 16, wherein the antenna is mounted to an outside surface of the implant.

18. The medical implant of claim 17, wherein the antenna is a serpentine antenna.

19. The medical implant of claim 16, further comprising a secondary coil circuit configured to be inductively coupled to a primary coil circuit to produce a DC voltage, wherein the DC voltage provides a supply voltage to the transmitter.

20. The medical implant of claim 16, further comprising:
   a secondary coil circuit configured to be inductively coupled to a primary coil circuit to produce a DC voltage; and
   a rechargeable voltage source configured to provide a supply voltage to the transmitter, wherein the DC voltage produced by the secondary coil circuit provides a recharging voltage to recharge the rechargeable voltage source.

21. The medical implant of claim 16, further comprising:
   a secondary coil circuit configured to be inductively coupled to a primary coil circuit to produce a DC voltage; and
   a cuff configured to receive a limb of a patient such that the cuff extends at least partially about the limb, the cuff carrying a primary coil of the primary coil circuit and configured to be positioned on the patient such that the primary coil and a secondary coil of the secondary coil circuit inductively couple while the primary coil is activated.

22. The medical implant of claim 16, further comprising a secondary coil circuit configured to be inductively coupled to a primary coil circuit to produce a DC voltage, wherein the primary coil circuit includes a primary coil and an excitation source electrically coupled to the primary coil, the excitation circuit producing an AC excitation signal at a frequency selected to ensure inductive coupling between the primary and secondary coils.

23. The medical implant of claim 16, further comprising an insulating layer positioned over the circuit board and configured to insulate the transmitter from biological material.

24. The medical implant of claim 16, wherein the sensor is selected from a group consisting of a temperature sensor, a load sensor, a strain sensor, and a torque sensor.

25. The medical implant of claim 16, wherein the circuit board is secured to the tibial tray using an electrically non-conductive adhesive.

26. The medical implant of claim 16, wherein the transmitter is configured to continually broadcast the sensor signal using the antenna.

27. An implantable bearing knee prosthesis, comprising:
a tibial tray having a platform with an elongated stem extending downwardly from a lower surface of the platform, the lower surface of the platform having a recess defined therein,
a circuit board positioned in the recess of the tibial tray;
a sensor mounted on the circuit board and configured to produce a sensor signal indicative of an operating condition of the implantable bearing knee prosthesis;
a memory unit mounted on the circuit board and electrically coupled to the sensor; and
a transmitter mounted to the circuit board and electrically coupled to the sensor and the memory unit, the transmitter configured to broadcast the sensor signal.

28. The implantable bearing knee prosthesis of claim 27, wherein the memory unit comprises a plurality of memory locations for storing sensor signals produced by the sensor.

29. The implantable bearing knee prosthesis of claim 27, wherein the memory unit has stored therein program code for controlling the operation of the transmitter.

30. The implantable bearing knee prosthesis of claim 27, further comprising an antenna electrically coupled to the transmitter and remotely located from the circuit board.

31. The implantable bearing knee prosthesis of claim 30, wherein the antenna is mounted to the orthopaedic implant.

32. The implantable bearing knee prosthesis of claim 27, further comprising a secondary coil circuit configured to be inductively coupled to a primary coil circuit to produce a DC voltage, wherein the DC voltage provides a supply voltage to the memory unit and to the transmitter.

33. The implantable bearing knee prosthesis of claim 27, further comprising:
a secondary coil circuit configured to be inductively coupled to a primary coil circuit to produce a DC voltage; and
a rechargeable voltage source configured to provide a supply voltage to the memory unit and the transmitter, wherein the DC voltage produced by the secondary coil circuit provides a recharging voltage to recharge the rechargeable voltage source.

34. The implantable bearing knee prosthesis of claim 27, further comprising:
a secondary coil circuit configured to be inductively coupled to a primary coil circuit to produce a DC voltage; and
a cuff configured to receive a limb of a patient such that the cuff extends at least partially about the limb, the cuff carrying a primary coil of the primary coil circuit and configured to be positioned on the patient such that the primary coil and a secondary coil of the secondary coil circuit inductively couple while the primary coil is activated.

35. The implantable bearing knee prosthesis of claim 27, further comprising a secondary coil circuit configured to be inductively coupled to a primary coil circuit to produce a DC voltage, wherein the primary coil circuit includes a primary coil and an excitation source electrically coupled to the primary coil, the excitation circuit producing an AC excitation signal at a frequency selected to ensure inductive coupling between the primary and secondary coils.

36. The implantable bearing knee prosthesis of claim 27, further comprising an insulating layer positioned over the circuit board and configured to insulate the transmitter and memory unit from biological material.

37. The implantable bearing knee prosthesis of claim 27, wherein the sensor is selected from a group consisting of a temperature sensor, a load sensor, a strain sensor, and a torque sensor.

38. The implantable bearing knee prosthesis of claim 27, wherein the circuit board is secured to the orthopaedic implant using an electrically non-conductive adhesive.

39. The implantable bearing knee prosthesis of claim 27, wherein the transmitter is configured to continually broadcast the sensor signal.

40. The implantable bearing knee prosthesis of claim 27, wherein the transmitter is configured to store the sensor signal in the memory unit.

41. The implantable bearing knee prosthesis of claim 40, wherein the transmitter is configured to broadcast the sensor signal after the sensor signal has been stored in the memory unit.

* * * * *